US011389283B2

(12) United States Patent
Montgomery et al.

(10) Patent No.: US 11,389,283 B2
(45) Date of Patent: Jul. 19, 2022

(54) FILTER AND OCCLUDER SYSTEMS AND ASSOCIATED METHODS AND DEVICES

(71) Applicant: W. L. Gore & Associates, Inc., Newark, DE (US)

(72) Inventors: William D. Montgomery, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 26 days.

(21) Appl. No.: 15/591,755

(22) Filed: May 10, 2017

(65) Prior Publication Data
US 2017/0325930 A1   Nov. 16, 2017

Related U.S. Application Data

(60) Provisional application No. 62/448,583, filed on Jan. 20, 2017, provisional application No. 62/334,767, filed on May 11, 2016.

(51) Int. Cl.
*A61F 2/01*     (2006.01)
*A61B 17/12*    (2006.01)
(Continued)

(52) U.S. Cl.
CPC ............ *A61F 2/01* (2013.01); *A61B 17/1215* (2013.01); *A61B 17/12036* (2013.01);
(Continued)

(58) Field of Classification Search
CPC ........ A61B 17/12109; A61B 17/12136; A61B 2017/1205; A61B 2090/3966;
(Continued)

(56) References Cited

U.S. PATENT DOCUMENTS 5,984,947 A    11/1999   Smith
6,558,405 B1*  5/2003   McInnes ................. A61F 2/013
                                                        606/200
(Continued)

FOREIGN PATENT DOCUMENTS

CN    101965161 A    2/2011
CN    104768476 A    7/2015
(Continued)

OTHER PUBLICATIONS

US 8,668,714, 04/1998, Siosteen (withdrawn)
(Continued)

*Primary Examiner* — Kelly J Bekker
*Assistant Examiner* — Andrew P. Restaino

(57) ABSTRACT

Various aspects of the instant disclosure relate to flow devices including filters and occluders for modifying flow in body conduits such as blood vessels. In some examples, such devices include a support structure and a flow media coupled to the support structure. The medical device generally further includes one or more capture features. In some examples, the capture features are coupled to the support structure at one or more of the proximal and distal ends of the support structure. In various examples, the capture features facilitate retrograde and antegrade deployment of the medical device and retrograde and antegrade capture of the medical device.

25 Claims, 8 Drawing Sheets

(51) Int. Cl.
   *A61M 25/09*      (2006.01)
   *A61B 90/00*      (2016.01)
(52) U.S. Cl.
   CPC .. *A61B 17/12109* (2013.01); *A61B 17/12136*
      (2013.01); *A61B 90/39* (2016.02); *A61M*
      *25/09* (2013.01); *A61B 2017/1205* (2013.01);
      *A61B 2090/3966* (2016.02); *A61F 2/011*
      (2020.05); *A61F 2002/016* (2013.01); *A61F*
      *2002/018* (2013.01); *A61F 2230/005*
      (2013.01); *A61F 2230/008* (2013.01)
(58) Field of Classification Search
   CPC .............. A61B 90/39; A61B 17/12036; A61B
      17/1215; A61B 17/12113; A61B
      17/12118; A61B 17/12122; A61B
      17/0057; A61B 2017/00575; A61B
      2017/00597; A61B 2017/00632; A61F
      2/01; A61F 2002/016; A61F 2002/018;
      A61F 2230/005; A61F 2230/008; A61F
      2/0108; A61F 2/011; A61F 2/013; A61F
      2/014
   USPC ........................................................ 606/200
   See application file for complete search history.

(56) References Cited

U.S. PATENT DOCUMENTS

| | | | |
|---|---|---|---|
| 7,763,044 B2 | 7/2010 | Inoue | |
| 7,771,452 B2 | 8/2010 | Pal | |
| 8,753,370 B2 | 6/2014 | Lashinski | |
| 9,839,517 B2* | 12/2017 | Centola | A61F 2/2445 |
| 2002/0095174 A1 | 7/2002 | Tsugita et al. | |
| 2003/0065355 A1* | 4/2003 | Weber | A61F 2/01 |
| | | | 606/200 |
| 2003/0130680 A1* | 7/2003 | Russell | A61F 2/0108 |
| | | | 606/200 |
| 2003/0139764 A1* | 7/2003 | Levinson | A61F 2/013 |
| | | | 606/200 |
| 2005/0015111 A1* | 1/2005 | McGuckin, Jr. | A61F 2/01 |
| | | | 606/200 |
| 2007/0112374 A1* | 5/2007 | Paul, Jr. | A61F 2/013 |
| | | | 606/200 |
| 2008/0147111 A1 | 6/2008 | Johnson | |
| 2009/0163926 A1 | 6/2009 | Sos | |
| 2009/0248060 A1* | 10/2009 | Schneider | A61F 2/0108 |
| | | | 606/200 |
| 2009/0326575 A1* | 12/2009 | Galdonik | A61F 2/01 |
| | | | 606/200 |
| 2010/0106178 A1* | 4/2010 | Obermiller | A61B 17/0057 |
| | | | 606/194 |
| 2012/0109179 A1 | 5/2012 | Murphy | |
| 2013/0022624 A1 | 1/2013 | Weaver et al. | |
| 2013/0204278 A1* | 8/2013 | Cully | A46B 3/18 |
| | | | 606/159 |
| 2013/0204347 A1 | 8/2013 | Armstrong et al. | |
| 2014/0052103 A1* | 2/2014 | Cully | A61B 17/221 |
| | | | 604/508 |
| 2014/0142609 A1* | 5/2014 | Keegan | A61F 2/013 |
| | | | 606/200 |
| 2014/0155929 A1 | 6/2014 | Belson | |
| 2014/0207174 A1* | 7/2014 | Hackett | A61F 2/01 |
| | | | 606/200 |
| 2014/0214072 A1 | 7/2014 | Eidenschink | |
| 2014/0236218 A1 | 8/2014 | Jantzen | |
| 2014/0243880 A1 | 8/2014 | Schotzko | |
| 2014/0243881 A1 | 8/2014 | Lees | |
| 2014/0260928 A1* | 9/2014 | Janardhan | A61F 2/01 |
| | | | 87/9 |
| 2015/0073470 A1* | 3/2015 | Andersen | A61F 2/01 |
| | | | 606/200 |
| 2015/0366649 A1* | 12/2015 | Tafti | A61F 2/01 |
| | | | 606/200 |
| 2016/0095688 A1* | 4/2016 | Johnsen | A61B 17/12109 |
| | | | 606/200 |
| 2016/0175083 A1 | 6/2016 | Johnson | |

FOREIGN PATENT DOCUMENTS

| | | |
|---|---|---|
| JP | 2003-513745 A | 4/2003 |
| WO | WO-2016049162 A1 | 3/2016 |

OTHER PUBLICATIONS

"Cerebral Protection Device Reduced Brain Lesions, Neurological Events After TAVR," Transcatheter Cardiovascular Therapeutics, published Sep. 13, 2014, 1 page.

Carpenter, Jeffrey P., "Reducing the risk of stroke and embolic lesions of TEVAR and TAVI with embolic protection devices," Vascular News, published Nov. 10, 2015, 3 pages.

Ellozy, Sharif H., MD, "Neurologic Protection During TEVAR," Endovascular Today, published Nov. 2014, 3 pages.

International Search Report and Written Opinion from PCT/US2017/032065, dated Jul. 21, 2017, 13 pages.

Kyokun Uehara, Novel detachable filter to prevent thromboembolism during endovascular surgery, The Journal of Thoracic and Cardiovascular Surgery, 2012, 1399-1403, 144(6), United States.

Leon, Martin B., MD, "Sentinel Dual Filter Device: Technology Overview and Status of CLEAN TAVI Randomized Trial" Transcatheter Cardiovascular Therapeutics, Columbia University Medical Center Cardiovascular Research Foundation New York City, Sep. 15, 2014, 33 pages.

Mieghem, Nocolas M. MD, "Strokes after TAVR II Management Considerations (Current and Future)," Transcatheter Cardiovascular Therapeutics, Columbia University Medical Center, Sep. 14, 2014, 25 pages.

* cited by examiner

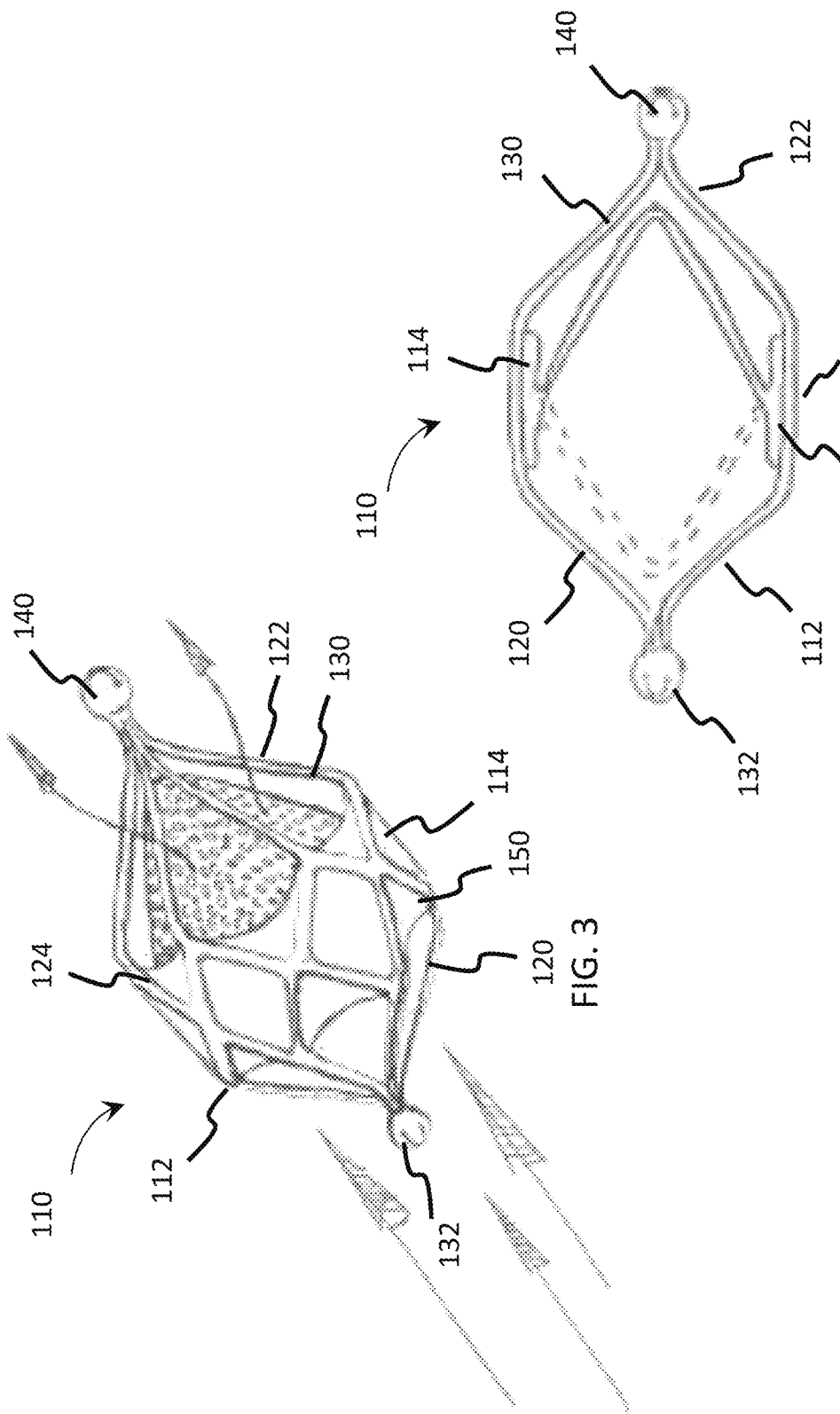

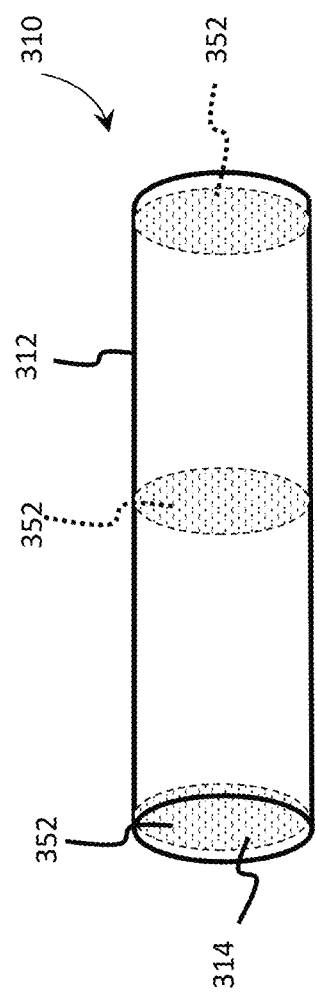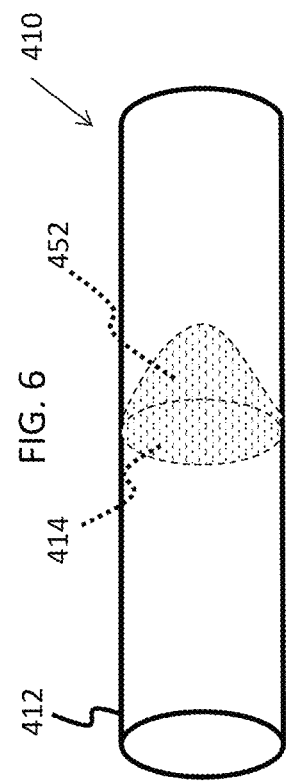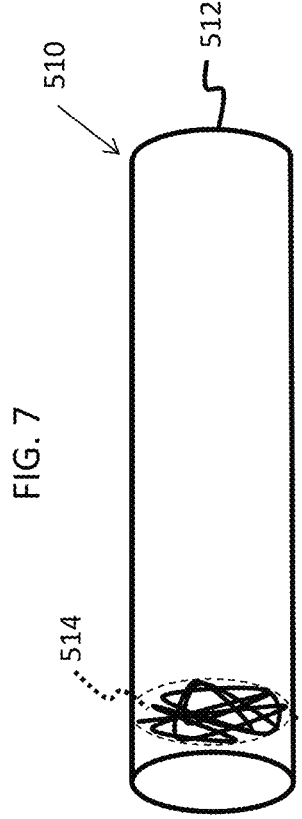

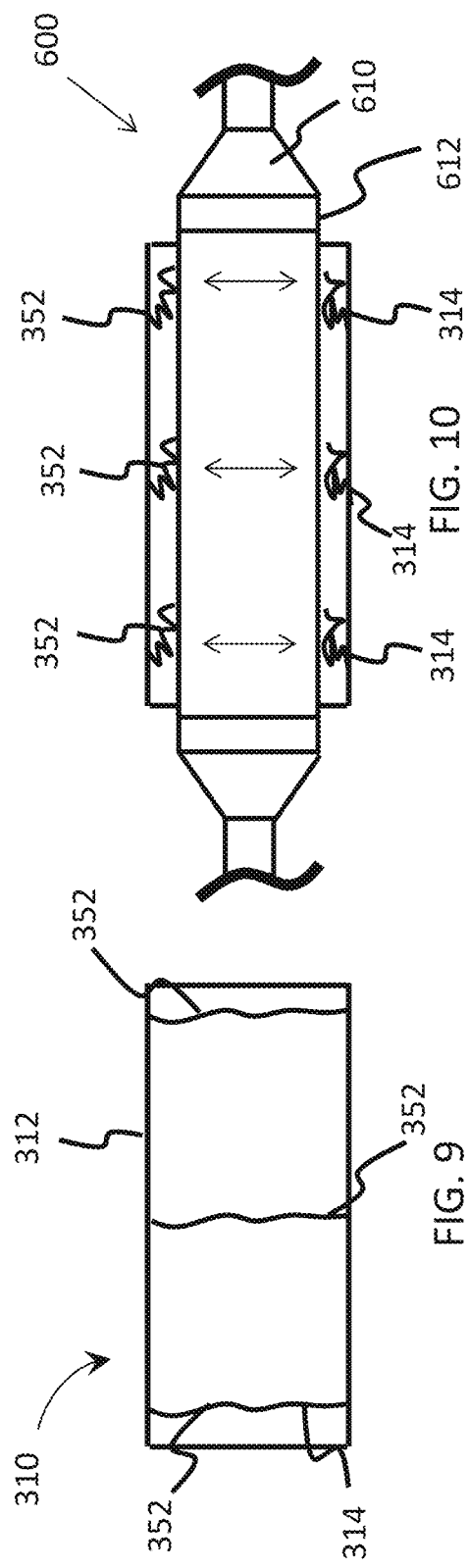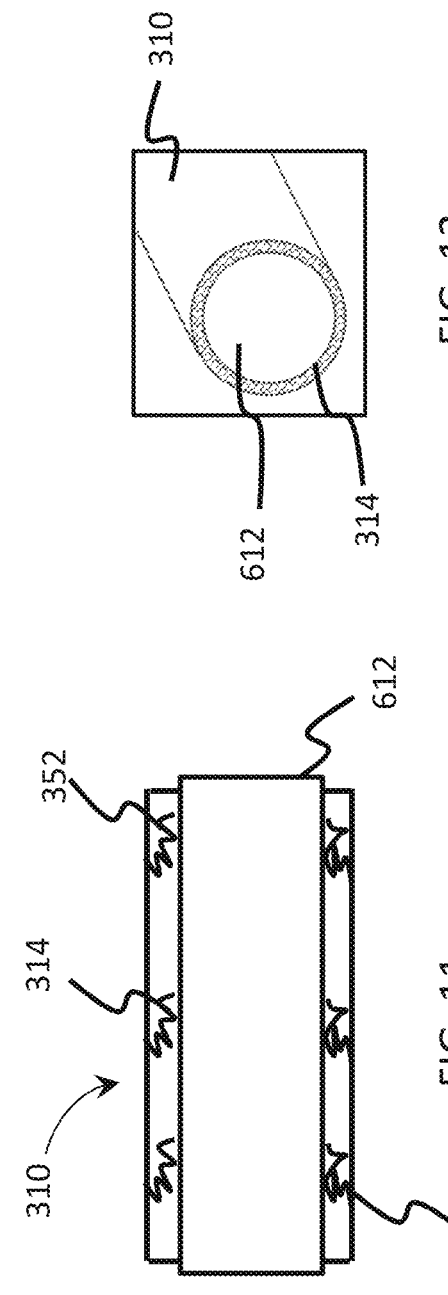

FILTER AND OCCLUDER SYSTEMS AND ASSOCIATED METHODS AND DEVICES

CROSS-REFERENCE TO RELATED APPLICATION

This application claims the benefit of U.S. Provisional Application 62/334,767, filed May 11, 2016, and also claims the benefit of U.S. Provisional application 62/448,583, filed Jan. 20, 2017, both of which are herein incorporated by reference in their entireties for all purposes.

SUMMARY

Various systems, methods, and devices according to the present disclosure are usable as flow devices, also described as filters or occluders, such terms being used interchangeably herein unless otherwise indicated by device application.

Some aspects of the disclosure relate to filters that remain patent for an extended period of time in comparison to traditional filters. Such filters may be applicable for protecting against embolic release during complex endovascular procedures or other filtration applications.

Some aspects of the disclosure relate to flow devices that remain patent for a desired period of and eventually become less patent and, if desired, fully or nearly fully occlusive over time. Such occluders may find use in a variety of applications, including techniques for reducing the patency of one or more blood vessels, apertures of grafts/stent-grafts, or branches of grafts/stent-grafts over time, as well as others.

Some aspects of the disclosure relate to flow devices that are capable of being collapsed and removed from the vasculature from either a distal or a proximal approach direction (e.g., antegrade or retrograde directions) to facilitate, for example, intravascular removal of the devices from different access locations.

Some aspects of the disclosure relate to flow devices that are bi-directionally deployable, where such devices can be deployed in a distal-to-proximal end or a proximal-to-distal end orientation to facilitate, for example, intravascular deployment of the devices from different access locations.

Some aspects of the disclosure relate to flow systems including a plurality of flow devices deployed and left in place to provide such advantages as enhanced protection against post-operative complications, including embolisms, for example.

Some aspects of the disclosure relate to methods of making and methods of treatment using the flow devices and systems described herein, including applications in which flow devices are implanted in the body for an extended period of time (e.g., including after conclusion of a primary treatment procedure, such as EVAR) and later retrieved from the body after a desired time period.

While multiple examples are disclosed, still other examples will become apparent to those skilled in the art from the following detailed description, which shows and describes illustrative examples. Accordingly, the drawings and detailed description are to be regarded as illustrative in nature and not restrictive.

BRIEF DESCRIPTION OF THE DRAWINGS

FIGS. 3 and 4 illustrate another flow device, according to some examples.

FIGS. 6-8 illustrates additional flow devices, according to some examples.

FIGS. 9-12 illustrate a flow device with a flow reversion device inserted and deployed in the flow device, according to some examples.

DETAILED DESCRIPTION

Various aspects of the instant disclosure relate to flow devices, also described as filters or occluders, for modifying flow (e.g., filtering, reducing, and/or occluding flow) in body conduits, such as blood vessels. In some examples, such devices achieve relatively low porosity while maintaining patency for desired periods of time, including extended periods of time following implantation and associated procedure cessation. Some examples of device applications include use for the prevention of stroke, ischemic bowel, reduced renal function, distal peripheral artery occlusion, internal iliac occlusion, inferior mesenteric occlusion, selective filtering and/or occluding of implant branches (e.g., stent graft branches) and others that this disclosure will make apparent, such as partial or total occlusion of the gastric arteries for the treatment of obesity.

Figures 1, 1A:
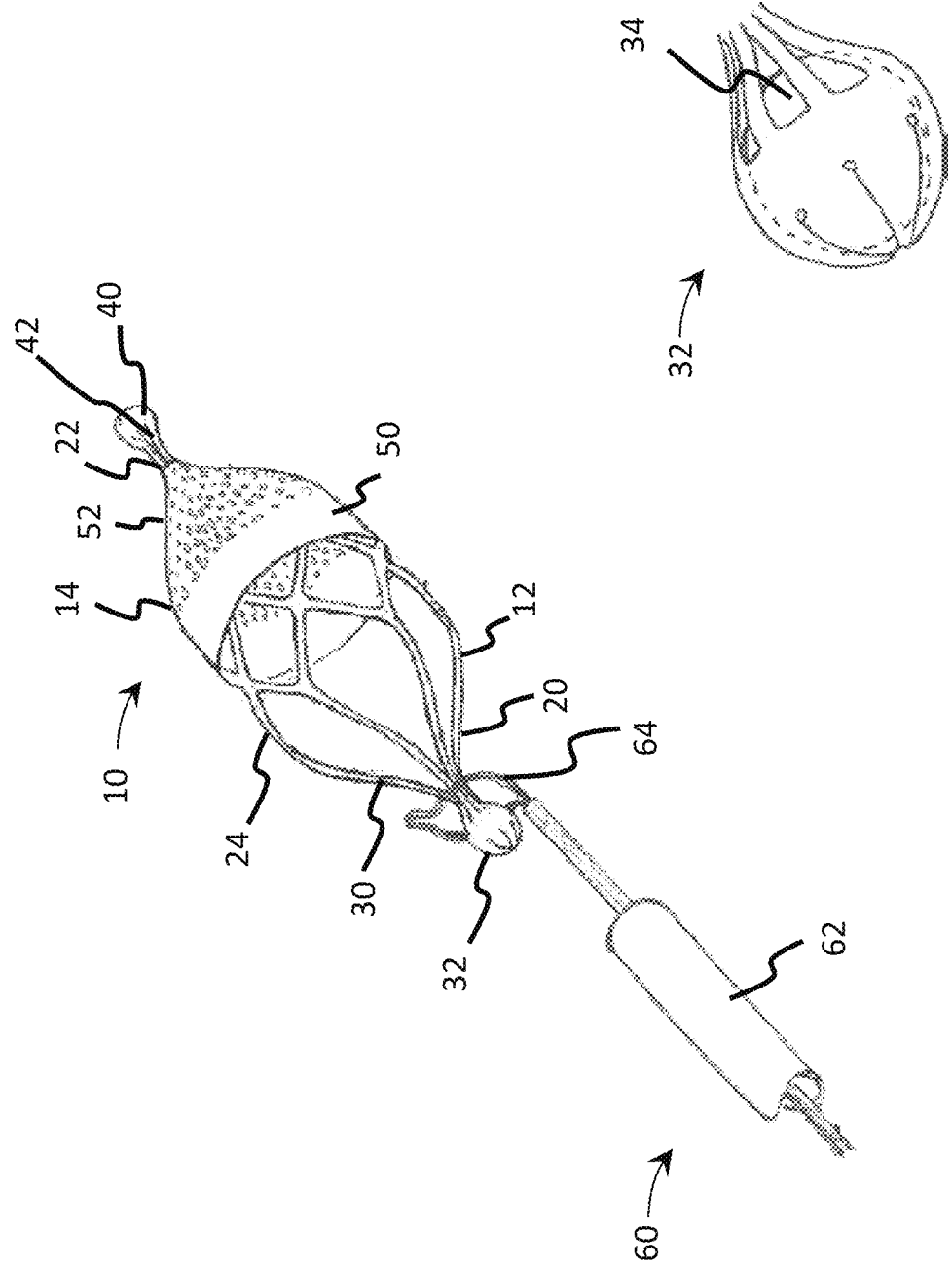
FIG. 1 illustrates a retrieval system and associated flow device, according to some examples.
FIG. 1A illustrates a portion of the flow device of FIG. 1, according to some examples.

FIG. 1 shows a flow device 10 and retrieval system according to some examples. As shown, the flow device 10 includes a support frame 12 and a flow media 14. The device 10 is configured for implantation in one or more body lumens and can have an outer diameter between 3 mm and 20 mm, although a variety of dimensions are contemplated.

The support frame 12, also described as a support structure, is optionally formed of a shape memory material, such as a nickel-titanium alloy, although a variety of materials, such as stainless steel or suitable polymeric materials are contemplated. If desired, the support frame 12 is formed as a cut tube (e.g., a laser cut tube) that is collapsible to an elongated, smaller diameter profile (not shown) for intraluminal deployment using a delivery system (e.g., a delivery catheter). If desired, the support frame 12 is optionally formed of discrete wires, for example using one or more mandrel wire forming operations. Although some examples are provided, a variety of frame shapes, materials, and manufacturing methods are contemplated, including those disclosed in U.S. Pat. No. 8,668,714 (Cully et al.), issued Mar. 11, 2014. In some examples, the support frame 12 is configured to self-expand or to be expanded (e.g., via balloon) to engage the wall of the body lumen into which it is deployed (e.g., against a blood vessel wall, such as the aortic arch) to anchor the device 10 in place.

As shown in FIG. 1, the support frame 12 includes a proximal portion 20, a distal portion 22 and an intermediate portion 24 between the proximal and distal portions 20, 22. As shown, the support frame 12 is generally formed of a plurality of frame members 30, also described as struts 30. The frame members 30 are optionally portions of a cut tube, discrete wires wound or coupled together, or of another design as desired. The support frame 12 is optionally self-expanding or expandable (e.g., balloon expandable) as desired.

The proximal portion 20 includes a first capture feature 32, and tapers conically away from the intermediate portion 24. An enlarged view of the capture feature 32 is shown in FIG. 1A.

As shown in FIG. 1A, the capture feature 32, also described as a coupling means 32, extends from the plurality of struts 30 and forms a generally spherical shape (e.g., round spherical), although a variety of shapes (e.g., oblong spherical) are also contemplated. In some examples, for example when formed by laser cutting, the capture feature (or capture element) includes one or more relief cuts to facilitate forming the capture feature 32 into a desired shape (e.g., similar to a bell, or "jingle bell"). Though largely obscured in FIG. 1A, a first radiopaque marker 34 (e.g., a discrete piece of radiopaque material) is optionally received and retained in the first capture feature 32. The first radiopaque marker 34 is optionally used to assist with placement of the device 10 during a deployment operation and/or to recover the device 10 during a recovery, or retrieval operation, for example.

As shown in FIG. 1, and though partially obscured by the flow media 14, the intermediate portion 24 of the support frame 12 is generally cylindrical in shape, although a variety of shapes (e.g., tapered, hourglass, dog bone, and others) are contemplated.

The distal portion 22 of the support frame 12 is shown in FIG. 1 largely covered by the flow media 14. In some examples, the distal portion 22 of the support frame 12 tapers conically to a second capture feature 40. As shown in FIG. 1, the tapered distal portion 22 supports the flow media 14 in a corresponding conical shape shown in FIG. 1. The second capture feature 40, also described as a coupling means 40, is optionally substantially similar to the first capture feature 32. For example, the second capture feature 40 can be similarly shaped and formed to the first capture feature 32 and also includes a second radiopaque marker 42, although a variety of configurations are contemplated. If desired, the first and second capture features 32, 40 and/or the first and second radiopaque markers 34, 42 are distinct from one another, for example having different radiopacities, shapes, materials, coatings, or otherwise being distinguishable from one another.

As shown in FIG. 1, the flow media 14 includes a first portion 50 received over an outside surface of the intermediate portion 24 of the support frame 12 and a second portion 52 received over the distal portion 22 of the support frame 12. The flow media 14 is optionally described as a porous fabric, where the term "porous fabric" is generally meant to indicate a layer of material configured to permit at least some level of fluid passage (having a desired fluid permeability) through one or more flow pathways or "pores" in the material.

As shown in FIG. 1, the first portion 50 is received outside of the intermediate portion 24. Though shown outside the intermediate portion 24, a variety of configurations are contemplated, including the first portion 50 being received on an inner surface of the intermediate portion 24, embedded with the intermediate portion 24, comprising multiple layers or parts sandwiching the intermediate portion 24, and others. In some examples, the first portion 50 of the flow media 14 is substantially continuous, where the first portion 50 may be substantially impermeable or permeable, or have any desired permeability to gases or water, blood, bile, or other bodily fluids as desired. In some examples, the first portion 50 is formed of one or more layers of expanded PTFE film adhered (e.g., by FEP applied to the film and/or support frame 12) or otherwise secured to the support frame 12 (e.g., by suturing, friction fit, or other means for securing).

According to some examples, the second portion 52 of the flow media 14, also described as the filtration portion 52 or flow control portion 52, includes a plurality of openings such that the second, or flow control portion 52 is permeable to fluid flow, for at least an initial desired time period. The flow control portion 52 is optionally configured to capture particulate or other substances in a fluid passing through the flow control portion 52. For example, with blood, it may be desirable to capture plaque debris, blood clot debris, or other content. As described in greater detail below, in some examples, one or more portions of the device 10 (e.g., the flow control portion 52) includes drug coatings, surface treatments (e.g., such as the surface treatment marketed under the tradename "CBAS" by W. L. Gore & Associates), or other modification(s) to facilitate a breakdown of material caught in the flow control portion 52.

In some examples, the device 10 is configured to be delivered "off-the-wire," without riding on a guidewire captured within a lumen of the device. However, as discussed further below, in some examples, one or more guidewires may be utilized during delivery of the device 10. In some examples, the device 10 can be deployed using well known intravascular catheter techniques from a compacted delivery profile to an expanded deployed profile. In at least this manner, the device 10 can be left in the body following a procedure or a portion of a procedure without the need of removing a guidewire from the device 10 and/or removing the device 10 with an associated treatment device, such as an associated balloon catheter or stent-graft deployment system. Moreover, multiple devices can be deployed from a single delivery system at different delivery sites using such an "off-the-wire" approach. Generally, push/pull delivery catheters, constraining sheaths, and other delivery systems are contemplated for deploying the devices as desired.

FIG. 1 also shows a capture system 60 including a guide catheter 62 and a snare catheter with a retractable loop 64. As indicated in FIG. 1, the capture system 60 is optionally used to capture the first capture feature 32 at which point the device can be withdrawn and collapsed into the guide catheter 62 or another collapsing feature for withdrawal or position adjustment of the device. Additionally, the capture system 60 or a similar capture system is optionally utilized to capture and retrieve the device 10 using the second capture feature 40. In other words, the device 10 configuration facilitates retrieval and removal and/or repositioning of the device 10 from either distal or proximal approaches, also described as ante- or retrograde approaches in terms of flow. Thus, a user of the device 10 and capture system 60 is able to approach the device from different vascular entry points, or directions within a body lumen, as desired.

FIGS. 2A-2F show a variety of potential configurations for the openings in the flow media 14, such as the flow control portion 52. Openings may be formed by removal processes (e.g., cutting or etching) films, sheets, membranes, or other materials. Openings may also be formed by weaving, knitting, or other techniques using individual or multi-fiber strands, or using other materials and/or methods as desired.

Figure 2A:
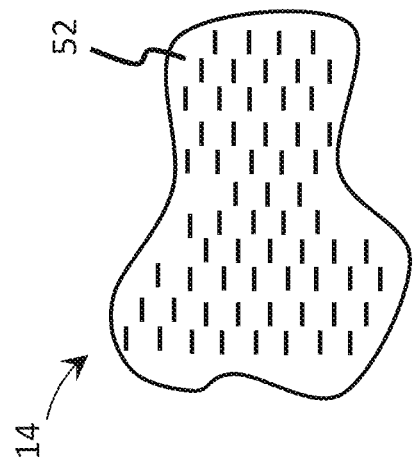
FIGS. 2A-2F illustrate flow media, according to some examples.
Figure 2C:
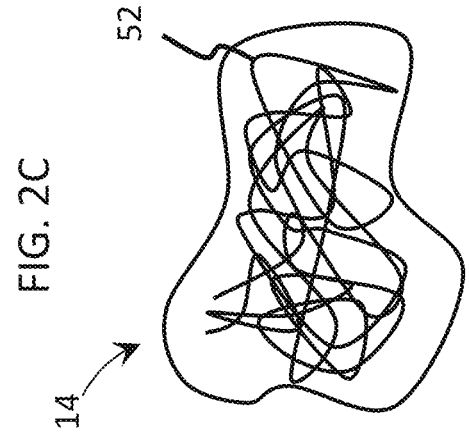
Figure 2B:
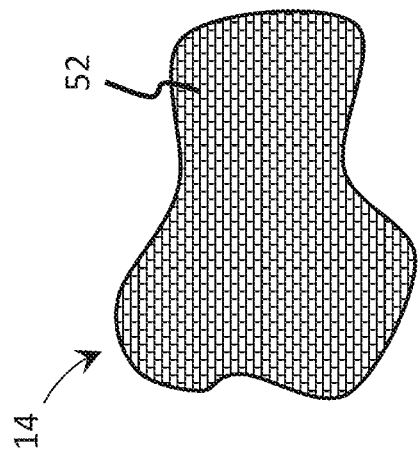
Figure 2F:
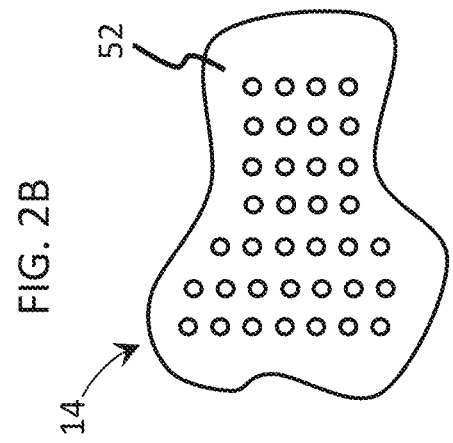
Figure 2D:
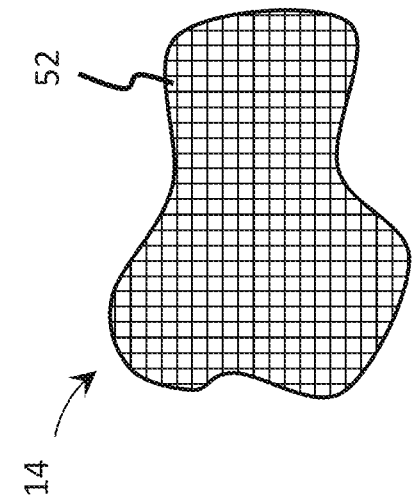
Figure 2E:
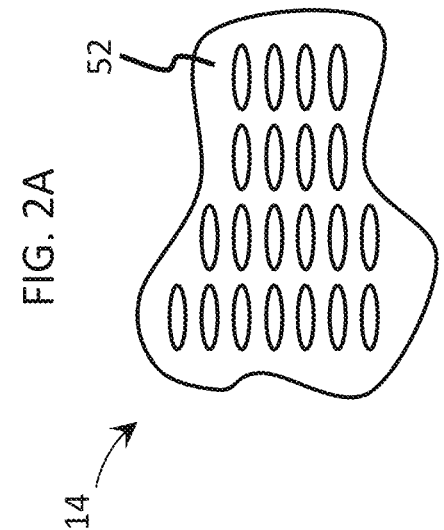

FIG. 2A shows a square lattice structure, such as those described in U.S. Pub. US 2013/0204347 ("Armstrong et al"), published Aug. 8, 2013 usable for the flow media 14. FIG. 2B shows a modified lattice structure in which the openings are offset and rectangular, according to some examples of one or more portions of the flow media 14 (e.g., flow control portion 52). FIG. 2C shows a series of slits with a desired length, depth, and separation; FIG. 2D shows a series of ovular, or oval-shaped openings of a desired length, width, number and separation; FIG. 2E shows generally round openings with a desired diameter and separation; and FIG. 2F shows a series of random, irregular openings formed by an irregular fibrous structure; each of the foregoing provide just a few examples of configurations of one or more portions of the flow media 14 (e.g., configurations of the flow control portion 52).

The openings generally define a porosity level of the flow media 14. For example, in some examples, the porosity level is defined as an average or maximum diameter or dimension of the openings being 500 microns, 400 microns, 300 microns, 200 microns, 100 microns, or other dimension. In some implementations (e.g., where occlusion is desirable), the porosity level is defined as an average or a maximum diameter or dimension of the openings being less than 100 microns, such as 50 microns, 10 microns, or 5 microns, for example. The porosity level can also be defined as the openings being configured to filter down to 500 micron, 400 micron, 300 micron, 200 micron, or 100 micron or other maximum or average particle size. In some implementations, (e.g., where occlusion is desirable), the porosity level of the flow media 14 is defined as the openings being configured to filter down to a maximum or average particle size of less than 100 micron particles sizes, such as 50 micron, 10 micron, or 5 micron particle sizes, for example.

In some examples, the flow control portion 52 is configured to remain at a desired patency level for a desired time period (e.g., minutes, hours, days, weeks, or months). In some examples, this facilitates use of the device 10 to remain implanted following completion of the primary procedure (e.g., EVAR) and to reduce the incidence of postoperative complications (e.g., stroke from embolic debris) by remaining in the body following completion of the procedure for a desired period (e.g., maintaining a desired patency for a period of between 12 hours and a 7 days). In some examples, this extended patency helps allow controlled occlusion of vessel and/or portion of an endovascular device (e.g., stent graft) to reduce issues (e.g., system circulatory issues) associated with immediate or near immediate occlusion of such pathways. For example, a more gradual occlusion or "low flow" occlusion may permit the body to accommodate such partially or reduced flow in the body vessel and thereby reduce negative physiologic impact.

The flow media 14 or a portion thereof (e.g., the flow control portion 52 of the flow media 14) is optionally provided with one or more treatments (e.g., the heparin-based treatment provided by W.L. Gore and Associates under the trade name "CBAS") to maintain device patency for a desired period of time. In some examples, the flow control portion 52 is formed of expanded PTFE material or other fluoropolymer, although any of a variety of biocompatible biomaterials are contemplated. Various adjustments can be made to the material as desired, including the number and type of material layers (e.g., expanded PTFE microstructure, density, layer-to-layer variations) and opening configurations (size, spacing, shape, and others) in order to achieve a desired patency, or flow vs. time profile for the device 10. In some examples, the desired patency is defined in terms of a minimum volumetric flow rate through the device 10 over the desired time period. The desired patency can also be described in terms of a minimum percentage of the initial volumetric flow rate exhibited by the device at the time of implantation over the desired time period (e.g., at around 100%, 90%, 80%, etc.).

FIGS. 3 and 4 show another flow device 110, according to some examples. FIG. 3 is an isometric representation and FIG. 4 is generally a side, partial sectional representation of the device 110. As shown, the device 110 includes various features similar to those of the device 10. For example, the device 110 includes a support frame 112 and a flow media 114. The support frame 112 also includes a proximal portion 120, a distal portion 122 and an intermediate portion 124 between the proximal and distal portions 120, 122. As shown, the support frame 112 is generally formed of a plurality of frame members 130, also described as struts 130. The frame members 130 are optionally portions of a cut tube, discrete wires wound or coupled together, or of another design as desired. The support frame 112 is optionally self-expanding or expandable (e.g., balloon expandable) as desired.

The proximal portion 120 is optionally conically tapered and extends to a first capture feature 132, also described as a coupling means.

As shown in FIGS. 3 and 4, the capture feature 132 is optionally substantially similar to the capture features (or capture elements) previously described in association with device 10, although a variety of designs are contemplated.

As shown in FIGS. 3 and 4, the intermediate portion 124 of the support frame 112 is generally cylindrical in shape, although a variety of shapes (e.g., tapered, hourglass, dog bone, and others) are contemplated.

As shown in FIGS. 3 and 4, the distal portion 122 of the support frame 112 tapers conically to a second capture feature 140. As described below, the proximal and distal portions 120, 122 receive the flow media 114 depending upon a position of the flow media 114 as dictated by flow direction.

The second capture feature 140 is optionally substantially similar to the second capture feature 40, although a variety of configurations are contemplated.

As shown in FIGS. 3 and 4, the flow media 114 includes a first portion 150 received on an inside surface of the intermediate portion 124 of the support frame 112. The first portion 150 is optionally substantially cylindrical, or tubular in shape. Though shown outside the intermediate portion 124, a variety of configurations are contemplated, including the first portion 150 being received on an outer surface of the intermediate portion 124, embedded with the intermediate portion 124, comprising multiple layers sandwiching the intermediate portion 124, and others. In some examples, the first portion 150 of the flow media 114 is substantially continuous, with the first portion 150 being substantially impermeable or permeable, or having any desired permeability to gases or water, blood, bile, or other bodily fluids as desired. In some examples, the first portion 150 is formed of one or more layers of expanded PTFE film adhered (e.g., by FEP applied to the film and/or support frame 112) or otherwise secured to the support frame 112 (e.g., by suturing, friction fit, or other securing means). As shown, the first portion 150 is generally cylindrical, or tubular in shape, although a variety of shapes are contemplated.

According to some examples, the second portion 152 of the flow media 114 is substantially conical in shape and is attached to the first portion 150 of the flow media (e.g., generally at the middle of the first portion, extending inwardly from the first portion 150). Similar to the flow control portion 52, the second portion 152, also referred to as the filtration portion 152 or flow control portion 152, includes a plurality of openings such that the flow control portion 152 is permeable to fluid flow for at least desired time period, according to some examples. The flow control portion 152 is modifiable similarly to the flow control portion 52 to achieve a desired patency, or flow vs. time profile for the device 110.

With the flow control portion 152 so configured, predominant flow is able to flip the flow control portion 152, or otherwise cause its configuration to mirror, in vivo. This feature, though not always necessary for such a bidirectional advantages, can provide the benefit of being able to implant the device 110 in either direction, without regard to whether the distal end or proximal end is pointing in the direction of flow. This, coupled with the ability to retrieve the device from either direction, provides even further benefits in the ability to deliver and/or retrieve the device 110 in antegrade or retrograde directions, for example. In particular, where the device 110 is pre-loaded with a delivery system (not shown) the ability to deliver the device 110 from either direction can be particularly advantageous as a user is not required to select a retro- or antegrade approach based upon the device orientation as assembled with the delivery system (not shown).

Figure 5A:
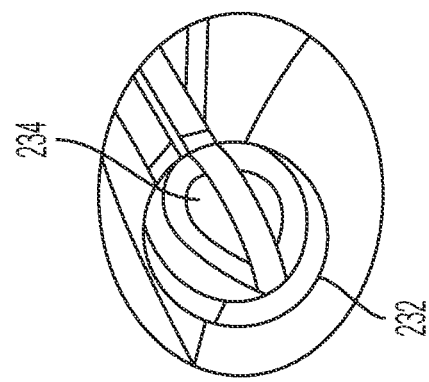
FIG. 5A illustrates a portion of the flow device of FIG. 5, according to some examples.
Figure 5:
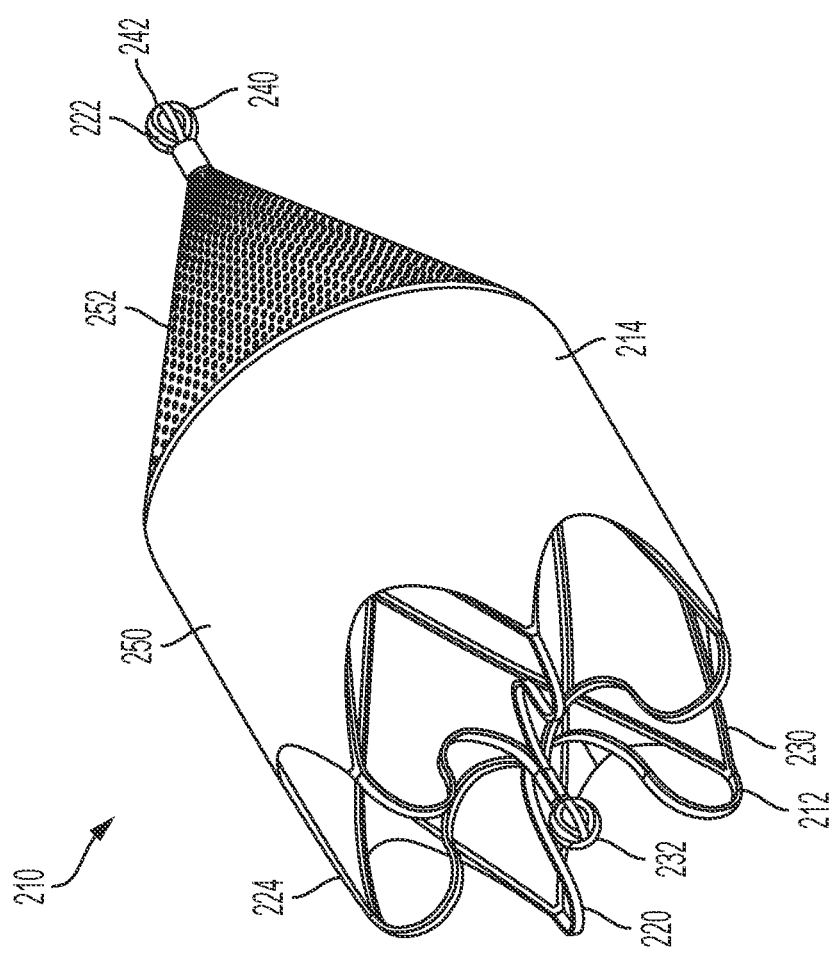
FIG. 5 illustrates another flow device, according to some examples.

FIGS. 5 and 5A show still another flow device 210 according to some examples. As shown in FIG. 5, the device includes a support frame 212 and a flow media 214. The support frame 212 includes a proximal portion 220, a distal portion 222 and an intermediate portion 224 between the proximal and distal portions 220, 222. As shown, the support frame 212 is generally formed of a plurality of frame members 230, also described as struts 230. The frame members 230 are optionally portions of a cut tube, discrete wires wound or coupled together, or of another design as desired. The proximal portion 220 includes a first capture feature 232, also described as a coupling means 232, and the struts 230 at the proximal portion 220 curve inwardly to define a recurved, or inverted framework. An enlarged view of the first capture feature 232 is shown in FIG. 5A. The support frame 212 is optionally self-expanding or expandable (e.g., balloon expandable) as desired.

As shown in FIG. 5A, the first capture feature 232 includes the plurality of struts 230 forming a generally spherical shape (e.g., round spherical), although a variety of shapes (e.g., oblong spherical) are also contemplated. Though largely obscured in FIG. 5A, a first radiopaque marker 234, (e.g., a discrete piece of radiopaque material) is optionally received and retained in the first capture feature 232. The first radiopaque marker 234 is optionally used to assist with placement of the device 210 during a deployment operation and/or to recover the device 10 during a recovery, or retrieval operation.

As shown in FIG. 5, and though largely obscured by the flow media 214, the intermediate portion 224 of the support frame 212 is generally cylindrical in shape, although a variety of shapes (e.g., tapered, hourglass, dog bone, and others) are contemplated.

The distal portion 222 of the support frame 212 is shown in FIG. 5 largely covered by the flow media 214. In some examples, the distal portion 222 of the support frame 212 tapers conically to a second capture feature 240. As shown in FIG. 5, the tapered distal portion 222 supports the flow media 214 in a corresponding conical shape shown in FIG. 5. The second capture feature 240 is optionally substantially similar to the first capture feature 232, the second capture feature 240 being similarly shaped and formed and also including a second radiopaque marker 242, although a variety of configurations are contemplated. If desired, the first and second capture features 232, 240 and/or the first and second radiopaque markers 234, 242 are distinct from one another, for example having different radiopacities, shapes, materials, coatings, or otherwise being distinguishable from one another.

As shown in FIG. 5, the flow media 214 includes a first portion 250 received over an outside surface of the intermediate portion 224 of the support frame 212 and a second portion 252. Though shown outside the intermediate portion 224, a variety of configurations are contemplated, including the first portion 250 being received on an inner surface of the intermediate portion 224, embedded with the intermediate portion 224, comprising multiple layers sandwiching the intermediate portion 224, and others. As shown in FIG. 5, the first portion 250 of the flow media 214 is substantially continuous and includes a scalloped edge. The first portion 250 may be substantially impermeable or permeable, or have any desired permeability to gases or water, blood, bile, or other bodily fluids as desired. In some examples, the first portion 250 is formed of one or more layers of expanded PTFE film adhered (e.g., by FEP applied to the film and/or support frame 212) or otherwise secured to the support frame 212 (e.g., by suturing, friction fit, or using other securing means).

Similarly to the devices 10 and 110, according to some examples, the second portion 252 of the flow media 214, also described as the filtration portion 252 or flow control portion 252, includes a plurality of openings such that the second, or flow control portion 252 is permeable to fluid flow for at least a desired time period. The flow control portion 252 is modifiable similarly to the flow control portions 52, 152 to achieve a desired patency, or flow vs. time profile for the device 210.

In the device 210, the capture portions 232, 240 are optionally used similarly to the capture portions 32, 132, 40, 140 for bi-directional retrievability of the device 210 following deployment in body lumen (e.g., blood vessel).

FIGS. 6, 7, and 8 show additional flow devices 310, 410, and 510 respectively. As shown in FIG. 6, the flow device 310 includes a support frame 312 and a flow media 314. The support frame 312 is optionally an expandable or self-expanding stent structure and the flow media 314 is generally similar to the flow media 14, 114, 214 previously described, although as shown the flow media 314 is generally disc-shaped and extends across the inner-lumen of the support frame 312. The flow media 314 includes a plurality of flow control portions 352, each positioned at a different longitudinal location along the support structure 312.

FIG. 7 shows the flow device 410 including a support frame 412 and a flow media 414. The support frame 412 is optionally an expandable or self-expanding stent structure and the flow media 414 is generally similar to the flow media 14, 114, 214, 314 previously described, although as shown the flow media 414 is generally conical, or dome-shaped and extends across the inner-lumen of the support frame 414. In some examples, the flow media 414 is capable of reversing or "flipping" in direction with flow, as described in association with other examples. As shown, the flow media 314 includes a single flow control portion 452 positioned at a single, intermediate position, although a variety of positions are contemplated.

FIG. 8 shows the flow device 510 including a support frame 512 and a flow media 514. The support frame 512 is optionally an expandable or self-expanding stent structure and the flow media 514 is generally similar to the flow media 14, 114, 214, 314, 414 previously described, although as shown the flow media 514 is a fibrous material (e.g., a fibrous mat or matrix) that extends across the inner-lumen of the support frame 512. As shown, the flow media 514 includes a single flow control portion 552 positioned at a single, proximal position, although a variety of positions are contemplated.

A variety of device designs and features have been disclosed. It should be understood that any combinations of any of the features from devices 10, 110, 210, 310, 410, 510 are contemplated.

FIGS. 9-10 illustrate a method of flow reversion, according to some examples, with reference to the device 310 although similar concepts may be applicable to one or more of the other flow devices described herein. FIG. 9 is a schematic view of the device 310 from a side view showing the support frame 312 and flow media 314. FIG. 10 shows a balloon catheter device 600 (e.g., a balloon catheter 610 with a deployable stent 612 received over the balloon 614 of the balloon catheter 610) pushed through the flow media 314 with the balloon 614 inflated and the secondary stent 612 pressing the flow media 314 against the inner wall of the support frame 312. FIG. 11 shows the balloon catheter removed and FIG. 12 is an end view of the device 310 with the secondary stent 612 reverted generally to the flow available prior to insertion and deployment of the device 310.

Some examples relate to a flow system comprised of multiple, independent flow devices that can be deployed on any of the branches of the aorta during endovascular aneurysm repair, including abdominal aortic aneurysm and thoracic aneurysms (EVAR and TEVAR), transcatheter aortic valve replacement (TAVR), patent foramen ovale (PFO) treatment, left atrial appendage occlusion (LAAO), structural heart treatments, atrial fibrillation treatments, and others. The flow devices of the systems are able to be left in the patient for extended periods and retrieved post procedure.

Some methods of treatment involve the use of multiple, independent, retrievable flow devices acting as embolic protection devices deployed in the arch vessels (e.g., for TEVAR and TAVR) and/or the visceral vessels (e.g., carotid artery, superior mesenteric artery, left and right renal arteries, and inferior mesenteric artery) in conditions where the risk of embolic debris is significant, for example. Retrieval post endovascular and/or surgical procedure is optionally accomplished utilizing a retrieval system (e.g., a snare retrieval system) such as those previously described.

Figure 13:
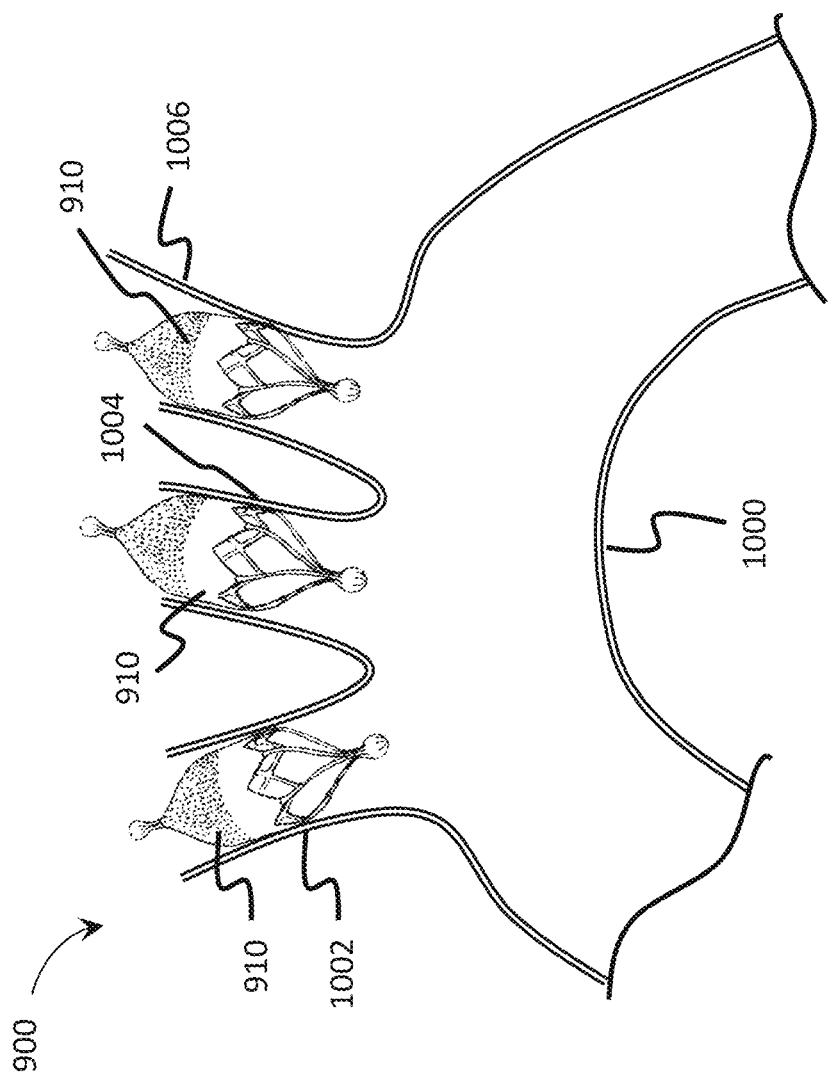
FIG. 13 illustrates a system of flow devices deployed in the aortic arch, according to some examples.

FIG. 13 shows a flow device system 900, deployed in a systemic treatment approach, according to some examples. FIG. 13 shows the aortic arch 1000 and its junctions with the brachiocephalic artery 1002, the left common carotid artery 1004, and the left subclavian artery 1006. As shown, a plurality of flow devices 910 similar to the flow device 10 are implanted in the arteries 1002, 1004, 1006 for systemic protection in association with a procedure, such as those previously described for treating the heart or aorta, for example. In some examples, the flow control portions of the devices 910 are placed near the ostia of the arteries 1002, 1004, 1006 to filter emboli out of the flow in the aortic arch 1000 and deflect emboli downstream, for example.

Any of the devices 10, 110, 210, 310, 410, 510, and combinations thereof, are contemplated for such applications. For example, although in the example of FIG. 13 the devices 910 are similar to device 10, in some examples, one more devices similar to device 510 are placed in one or more of the arteries 1002, 1004, 1006 with the flow control portion 552 oriented toward the vessel ostia. For example, in some examples, the flow control portion 552 includes a fibrous material that extends across the inner-lumen of the support frame 512, having the fibers of the flow control portion 552 oriented as desired relative to blood flow (e.g., generally perpendicular or oblique to the direction of flow). In other examples, the flow control portion 552 includes one or more portions similar to other designs previously described.

As discussed above, in some examples, the flow devices may be configured to be delivered "off-the-wire." That is, in some examples, the flow devices are configured to be delivered to a treatment site within a patient's vasculature without riding on a guidewire captured within a lumen of the device. However, as mentioned above, in some examples, one or more guidewires may be utilized during delivery of the flow devices disclosed herein.

Figure 14:
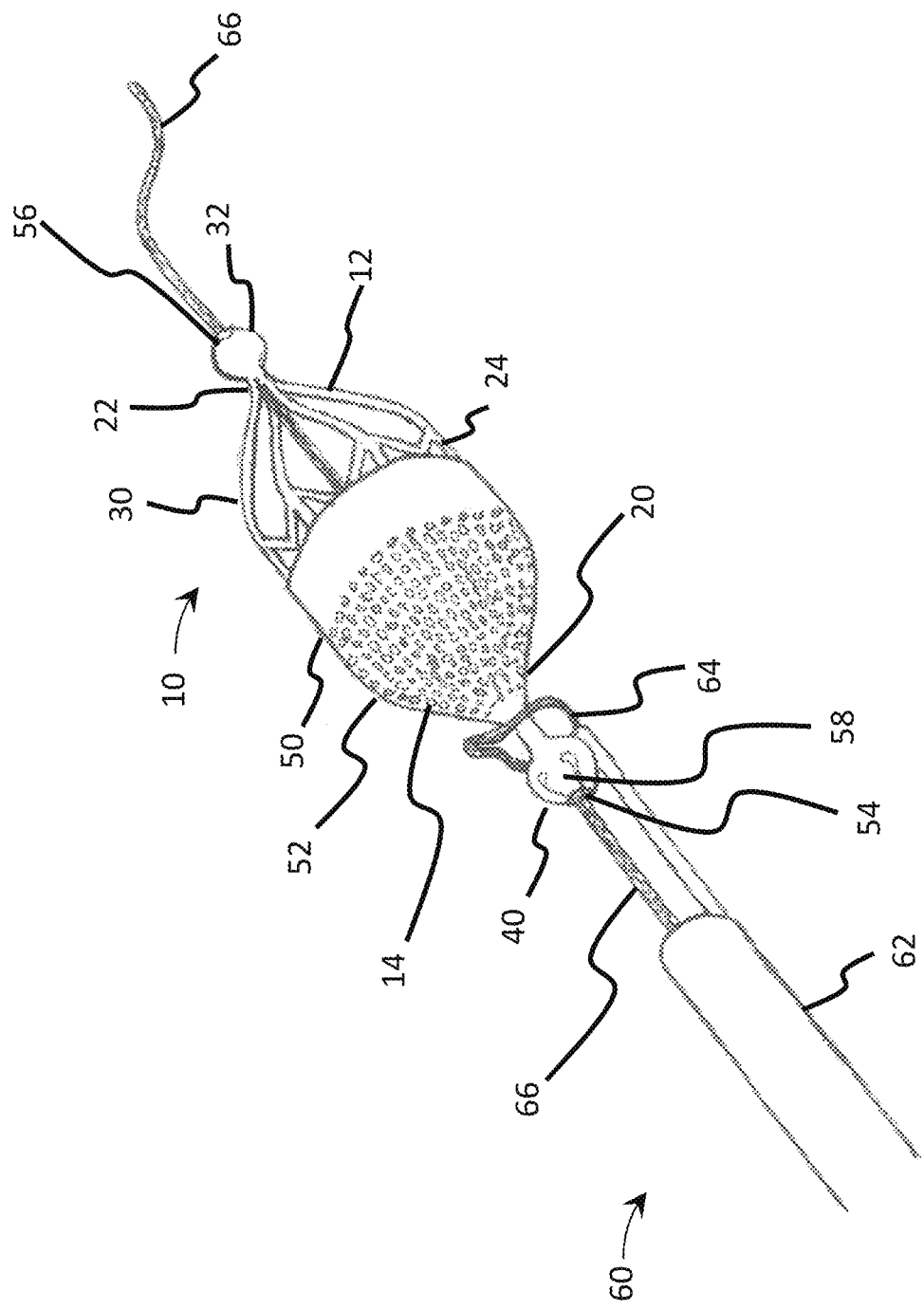
FIG. 14 illustrates a retrieval system and associated flow device, according to some examples.

Turning now to FIG. 14, a flow device 10 (similar to flow device 10 discussed above) is configured to be deliverable along a guidewire 66. In some examples, one or more apertures are formed in the device 10 such that the device 10 can be translated along a guidewire during delivery to the target site. The exemplary flow device 10 illustrated in FIG. 14 includes a first aperture 54 formed in the capture feature 40 and a second aperture 56 formed in the capture feature 32.

Those of skill in the art will appreciate that, similar to the off-the-wire examples discussed herein, such devices may alternatively be delivered to a treatment site along a guidewire and deployed using well known intravascular catheter techniques from a compacted delivery profile to an expanded deployed profile. In some examples, upon delivery and deployment, the guidewire can be subsequently removed from the device and such devices can be left in the body following a procedure or a portion of a procedure. That is, in some examples, the guidewire may be removed such that the device may remain implanted for a desired period (e.g., maintaining a desired patency for a period of between 0.5 hours and 7 days) following completion of a procedure (e.g., TEVAR). As explained above, such an approach may reduce the incidence of postoperative complications (e.g., stroke from embolic debris).

In examples where radiopaque markers are situated or received and retained by the capture features (or capture elements), one or more lumens may be formed through such radiopaque markers such that the device 10 can be delivered along the guidewire 66. Those of skill in the art will appreciate that such lumens can be formed in radiopaque markers without significantly diminishing the radiopacity of the radiopaque marker. In some examples, a single lumen may be formed through a radiopaque marker. In some other examples, a number of lumens may be formed through a radiopaque marker. In some examples, forming a plurality of lumens through a radiopaque marker may assist with the ease of loading the device on the guidewire. Thus, in some examples where a single lumen is formed in a radiopaque marker, it may be beneficial to fix a relative orientation of the radiopaque marker and the capture feature (or capture element) within which it is received. In some such examples, the radiopaque marker may be prevented from rotating or rolling within the capture feature (or capture element).

Although the device 10 illustrated in FIG. 14 is shown with the guidewire 66 extending thorough each of capture features 32 and 40, in some examples, the device may be loaded on the guidewire such that the guidewire extends through a subset or less than all of the capture features (or capture elements) of the device. For example and with reference to the device 10 illustrated in FIG. 14, in some instances, the device 10 may be loaded onto the guidewire 66 such that the guidewire 66 extends through the first capture feature 32 or second capture feature 40, but not both. In some such examples, a flow device may be loaded on the guidewire such that the flow device extends through only a distally located capture feature (or capture element), or alternatively only a proximally located capture feature (or capture element). Similarly, it should be appreciated that the flow devices disclosed herein may be loaded on the guidewire in either of a distal-to-proximal orientation or a proximal-to-distal orientation. That is, in some examples, the flow devices may be reversibly loaded on the guidewire.

Those of skill should appreciate that such a configuration provides versatility in that the devices may be deliverable from either an antegrade or retrograde direction. In various examples, the flow devices disclosed herein may be loaded on any commercial over the shelf guidewire.

As discussed above, in some examples where the device is delivered over a guidewire, the guidewire may be removed from the device after the device is delivered and deployed. In some other examples, upon deployment of the device, the device becomes secured at its position along the guidewire. Specifically, in some examples, upon deployment the capture features (or capture elements) through which the guidewire extends secure the guidewire therein. In some examples, the capture features (or capture elements) include one or more guidewire engagement elements that are configured to interface with the guidewire upon deployment of the device. For example, as shown in FIG. 14 second capture feature 40 includes a plurality of guidewire engagement elements 58. In some examples, prior to deployment of the device, the guidewire engagement elements are disengaged from the guidewire such that the device can be translated along the guidewire. That is, prior to deployment of the device, the guidewire engagement elements do not operate to secure the device against axial translation the guidewire. However, in these examples, upon deployment of the device, the engagement features engage the guidewire and operate to obstruct or otherwise prevent the device from being further axially translated along the guidewire. In some examples, upon retrieval of the device, the device is collapsed to its pre-deployment configuration wherein the guidewire engagement elements are disengaged from the guidewire such that the device can be translated along the guidewire. In some other examples, the guidewire engagement elements remain engaged with the guidewire even after the device is collapsed to its pre-deployment configuration. In some such examples, the guidewire can be utilized to draw the device into a retrieval sheath or allow for a snare to be advanced over the existing guidewire to capture the device by snaring a capture feature (or capture element) and subsequently drawing the device into a retrieval sheath (such as a guide catheter as discussed herein) as will be appreciated by those of skill in the art.

In some examples, the device is configured such that it is operable to be delivered in either an off-the-wire configuration or an over-the-wire configuration. Specifically, the device may be delivered off-the-wire despite being adapted or otherwise configured to be loaded onto and delivered via a guidewire. Indeed, in some examples, a device may be configured for delivery over a guidewire yet be delivered off-the-wire. In some examples where the device is configured to be loaded on and delivered via a guidewire, the lumens extending through the capture features (or capture elements) are generally configured such that debris captured by the flow media is not free to escape therethrough. In some examples, one or more one-way valves (e.g., such as one-way hemostatic valves) are integrated into the device such that captured debris is obstructed from escaping from the flow media through the lumens. In some examples, the filter media includes a guidewire lumen that is configured to accommodate the guidewire passing therethrough. In some examples, the filter media extends into a guidewire lumen extending through one or more components or portions of the device (such as the aperture or lumen extending through the capture feature, as explained below), wherein the guidewire lumen is collapsible or blockable (as discussed below).

In some examples, the one-way valve operates to allow a guidewire to pass through the device (such as through one or more of the lumens of the capture features or other lumens of the device). In some examples, one or more one-way valves are positioned adjacent the filter media. In some such examples, the one or more one-way valves are positioned in or proximate to the lumens of the capture features (or capture elements). In some examples, a one-way valve is incorporated into the capture feature or the lumen thereof. In some examples, the capture feature itself operates as a one-way valve. In some such examples, the one or more guidewire engagement elements of the capture feature (or capture element) may be multipurposed in that they operate to secure the capture feature (and thus the device) to the guidewire (as explained above) and additionally operate together to obstruct debris from escaping through the aperture formed therein when the guidewire is not otherwise extending therethrough.

In some examples, in addition to blocking debris from escaping from the filter media, one or more of the one or more one-way valves engage the guidewire such that the device is obstructed from translating along the wire (as discussed above). Thus, in some examples, a one-way valve may be multipurposed to block the escape of debris (such as embolic debris) as well as secure the device to the guidewire.

In some examples, one-way valves may be incorporated distally, proximally, or both distally and proximally of the filter media (also described as ante- or retrograde in terms of flow). Thus, it will be appreciated that the device may include a single one-way valve, or multiple one-way valves. In some examples where a single one-way valve is incorporated into the device, the single one-way valve may be positioned relative to the filter media such that the one-way valve is further antegrade (or downstream relative to the heart).

In some examples, one or more tension springs or other resilient members operate to secure the device to the guidewire. In some examples, the capture feature (or capture element) includes one or more tension springs that operate to cause the capture feature to engage the wire such that the device is obstructed from translating along the wire (as discussed above). In some examples, the one or more tension springs additionally or alternatively operate to constrict, collapse, or otherwise block the lumen or aperture extending through the capture features (or capture elements) when the guidewire is removed therefrom. In some examples, as mentioned above, the filter media extends into such lumens, and when the resilient member(s) cause the lumen to collapse, the debris remains captured by the filter media.

Additionally, in some examples, one or more elastic membranes, silicone grommets, and/or flapper valves may be utilized to prevent debris from escaping from the filter media through a guidewire lumen therein (as mentioned above). In some examples, such components operate to close with impinging flow Although various examples of applications of the devices described herein and associated systems have been described it should be apparent that any of applications are contemplated. Various modifications and additions can be The following is claimed:

1. A medical device comprising:
   a support structure that is collapsible, includes a plurality of struts, and has a proximal end, a distal end, and an intermediate portion located therebetween;
   a flow media attached to an inside of the support structure and comprising a portion configured to flexibly and reversibly extend from the intermediate portion toward the proximal end or the distal end of the support structure while hinging on the intermediate portion according to flow direction; and
   a proximal capture feature coupled to the proximal end of the support structure and a distal capture feature coupled to the distal end of the support structure, the proximal and distal capture features facilitating deployment of the medical device and capture of the medical device, wherein at least one of the proximal and distal capture features is substantially spherical.

2. The medical device of claim 1, further comprising a snare catheter with a loop, the proximal capture feature captured by the loop.

3. The medical device of claim 1, wherein the flow media is configured to filter fluid flowing through a vessel.

4. The medical device of claim 3, wherein the flow media includes a first side and a second side and is attached to the support structure such that either the first side or the second side of the flow media is adapted to filter fluid flowing through the flow media.

5. The medical device of claim 3, wherein the flow media includes pores having an average size ranging between 100 and 500 micrometers and a patency in the range of between 12 hours and 7 days.

6. The medical device of claim 1, wherein the flow media is configured to occlude fluid flowing through a vessel.

7. The medical device of claim 6, wherein the flow media includes pores having an average size of less than 100 micrometers and a patency configured to provide a gradual occlusion of a vessel.

8. The medical device of claim 1, wherein the flow media is formed from a polymeric material.

9. The medical device of claim 1, wherein the support structure includes an inner lumen and the flow media comprises a porous fabric and is attached to the support structure such that it extends across the inner lumen.

10. The medical device of claim 1, wherein the support structure is formed from a cut tube.

11. The medical device of claim 1, the distal capture feature comprising an aperture allowing the distal capture feature to be arranged over a guidewire.

12. The medical device of claim 1, wherein the plurality of struts and the at least one of the proximal and distal capture features are integrally formed portions of a single tubular member.

13. The medical device of claim 1, wherein at least one of the proximal end or the distal end defines a conical portion of the support structure that tapers longitudinally away from the intermediate portion.

14. The medical device of claim 13, wherein the flow media extends from the intermediate portion toward the conical portion such that the flow media is supported within the conical portion of the support structure.

15. A medical system comprising:
   a medical device including:
      a support structure including a plurality of struts, having a first end, a second end, and an intermediate portion located therebetween;
      a flow media attached to an inside of the support structure and comprises a portion configured to flexibly and reversibly extend from the intermediate portion toward the first end or the second end of the support structure while hinging on the intermediate portion according to flow direction; and
      a proximal capture feature and a distal capture feature, the proximal and distal capture features facilitating deployment of the medical device and capture of the medical device, and at least one of the proximal and distal capture features being substantially spherical;
   a catheter configured to receive the medical device therein; and
   a snare configured to engage either of the proximal capture feature and the distal capture feature such that the medical device is retrievable from both an antegrade direction and a retrograde direction.

16. The medical system of claim 15, further comprising a guidewire, the medical device received on the guidewire.

17. The medical system of claim 16, wherein the guidewire extends through at least one of the proximal and distal capture features.

18. The medical system of claim 16, wherein at least one of the proximal and distal capture features is configured to releasably engage the guidewire such that the medical device can be translated along the guidewire prior to deployment of the medical device and such that the medical device is constrained against translation along the guidewire upon deployment of the medical device.

19. The medical system of claim 15, the proximal capture feature comprising a lumen allowing the proximal capture feature to be arranged over a guidewire.

20. A medical device comprising:
   a support structure that is collapsible, includes a plurality of struts, has a proximal end, a distal end, and an intermediate portion located therebetween;
   a flow media attached to an inside of the support structure and comprises a portion configured to flexibly reverse direction between extending toward the proximal end or the distal end of the support structure according to a change in flow direction; and
   a distal capture feature at the distal end of the support structure, the distal capture feature facilitating antegrade deployment of the medical device and antegrade capture of the medical device, and the distal capture feature being substantially spherical.

21. A medical device comprising:
   a support structure that is collapsible, includes a plurality of struts, and has a first end, a second end, and an intermediate portion located therebetween;
   a flow media attached to the support structure, the flow media being conical or dome-shaped and configured to reversibly extend from the intermediate portion toward the first end or the second end of the support structure while within a body lumen;
   a first capture feature at the first end of the support structure and a second capture feature at the second end of the support structure, the first and second capture features facilitating deployment of the medical device and recapture of the medical device following deployment, wherein the first capture feature defines an interior space; and a radiopaque marker enclosed within the interior space of the first capture feature.

22. A medical system comprising:
a medical device including:
   a support structure including a plurality of struts, having a first end, a second end, and an intermediate portion located therebetween;
   a flow media attached to the support structure, the flow media being conical or dome-shaped and configured to reversibly extend from the intermediate portion toward the first end or the second end of the support structure while within a body lumen; and
   a first capture feature and a second capture feature, the first and second capture features facilitating deployment of the medical device and recapture of the medical device following deployment, and
   a radiopaque marker enclosed within the first capture feature;
a catheter configured to receive the medical device therein; and
   a snare configured to engage the first capture feature and the second capture feature such that the medical device is retrievable from both an antegrade direction and a retrograde direction.

23. A medical device comprising:
a support structure that is collapsible, includes a plurality of struts, and has a proximal end, a distal end, and an intermediate portion located therebetween, wherein at least one of the proximal end or the distal end defines a conical portion of the support structure that tapers longitudinally away from the intermediate portion; and
a flow media attached to and configured to reversibly hinge on the intermediate portion of the support structure, wherein the flow media extends from the intermediate portion and is configured to be positioned toward the conical portion such that the flow media is supported within the conical portion of the support structure or positioned away from the conical portion as dictated by flow direction.

24. A medical device comprising:
a support structure that is collapsible, includes a plurality of struts, and has a proximal end, a distal end, and an intermediate portion located therebetween, wherein at least one of the proximal end or the distal end defines a conical portion of the support structure that tapers longitudinally away from the intermediate portion; and
a flow media attached to the support structure, wherein the flow media extends from the intermediate portion and is configured to be reversibly positioned toward the conical portion such that the flow media is supported within the conical portion of the support structure or positioned away from the conical portion as dictated by a change in flow direction.

25. A medical device comprising:
a support structure that is collapsible, includes a plurality of struts, and has a proximal end, a distal end, and an intermediate portion located therebetween, wherein at least one of the proximal end or the distal end defines a conical portion of the support structure that tapers longitudinally away from the intermediate portion; and
a flow media attached to the support structure, wherein the flow media extends from the intermediate portion and is configured to be reversibly positioned toward the conical portion such that the flow media is supported within the conical portion of the support structure or positioned away from the conical portion as dictated by flow direction while within a body lumen.

* * * * *